(12) United States Patent
Kutzer et al.

(10) Patent No.: US 11,699,520 B2
(45) Date of Patent: Jul. 11, 2023

(54) CONTROL UNIT FOR A MEDICAL IMAGING SYSTEM COMPRISING A PROCESSOR AND A LOGIC GATE; IMAGING SYSTEM AND METHOD FOR CONTROLLING A MEDICAL IMAGING SYSTEM

(71) Applicant: Siemens Healthcare GmbH, Erlangen (DE)

(72) Inventors: Philipp Kutzer, Herzogenaurach (DE); Georg Weber, Fuerth (DE)

(73) Assignee: Siemens Healthcare GmbH, Erlangen (DE)

( * ) Notice: Subject to any disclaimer, the term of this patent is extended or adjusted under 35 U.S.C. 154(b) by 787 days.

(21) Appl. No.: 16/682,353

(22) Filed: Nov. 13, 2019

(65) Prior Publication Data
US 2020/0160990 A1  May 21, 2020

(30) Foreign Application Priority Data
Nov. 20, 2018  (DE) .......................... 102018219878.0

(51) Int. Cl.
*G05B 19/4155* (2006.01)
*G16H 30/20* (2018.01)
*G16H 40/63* (2018.01)

(52) U.S. Cl.
CPC ......... *G16H 40/63* (2018.01); *G05B 19/4155* (2013.01); *G16H 30/20* (2018.01); *G05B 2219/45169* (2013.01)

(58) Field of Classification Search
CPC ..... G16H 40/63; G16H 30/20; G05B 19/4155
(Continued)

(56) References Cited

U.S. PATENT DOCUMENTS 10,342,507 B2 *  7/2019  Tanaka ............... H04N 1/00095
2004/0015079 A1 *  1/2004  Berger ................. A61B 8/0841
600/443
(Continued)

FOREIGN PATENT DOCUMENTS

CN  206962733  *  2/2018
CN  107847213 A  *  3/2018  ........... A61B 8/4411
(Continued)

OTHER PUBLICATIONS

Andres Cicuttin; A Programmable System-on-Chip Based Digital Pulse Processing for High Resolution X-Ray Spectroscopy; IEEE: 2016; pp. 520-525.*
(Continued)

*Primary Examiner* — Monjur Rahim
(74) *Attorney, Agent, or Firm* — Harness, Dickey & Pierce, P.L.C.

(57) ABSTRACT

A control unit is for a medical imaging system. The control unit includes a programmable logic gate, designed for at least one of closed-loop control and open-loop control of at least one component of the medical imaging system; a microprocessor, connected to the programmable logic gate via a first interface; and a signal line to connect the microprocessor to a contact array, arranged externally on the control unit. The microprocessor is designed to provide a second interface via the signal line and to control the programmable logic gate in accordance with a command signal received via the second interface. Further, the signal line is provided at least in part by the programmable logic gate and the programmable logic gate includes a receive unit for reading out the command signal.

21 Claims, 3 Drawing Sheets

(58) Field of Classification Search
USPC .......................................................... 726/23
See application file for complete search history.

(56) References Cited

U.S. PATENT DOCUMENTS

| | | | |
|---|---|---|---|
| 2004/0017224 | A1 | 1/2004 | Turner et al. |
| 2012/0265071 | A1* | 10/2012 | Berke ..................... A61B 34/32 |
| | | | 600/439 |
| 2014/0103346 | A1* | 4/2014 | Yamazaki ......... H01L 29/41733 |
| | | | 257/66 |
| 2016/0066775 | A1* | 3/2016 | Hunter ................. A61B 1/0638 |
| | | | 600/178 |
| 2016/0166227 | A1* | 6/2016 | Tanaka ................... A61B 6/563 |
| | | | 382/132 |
| 2017/0014094 | A1* | 1/2017 | Hiroshige ................ A61B 6/42 |
| 2018/0078222 | A1* | 3/2018 | Boettger .............. G05B 19/048 |
| 2020/0108412 | A1* | 4/2020 | Greenberg ............ B06B 1/0215 |

FOREIGN PATENT DOCUMENTS

| | | | |
|---|---|---|---|
| DE | 202015002867 U1 | 5/2015 | |
| DE | 102016218138 A1 | 3/2018 | |
| DE | 202018002830 U1 | 10/2018 | |
| KR | 20170101634 | * | 9/2017 |

OTHER PUBLICATIONS

German Office Action for German Application No. 102018219878.0 dated Jun. 28, 2019.

\* cited by examiner

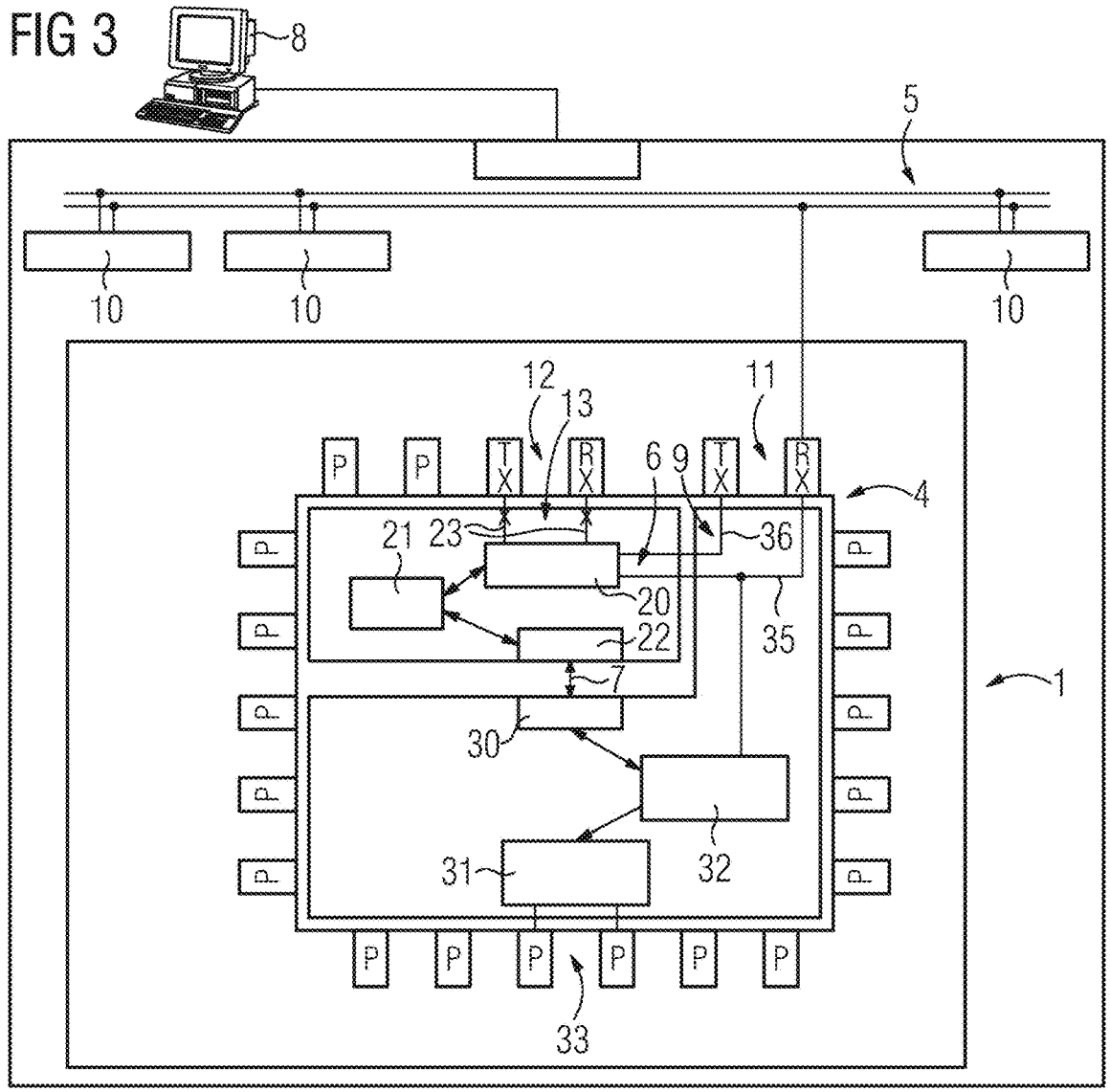
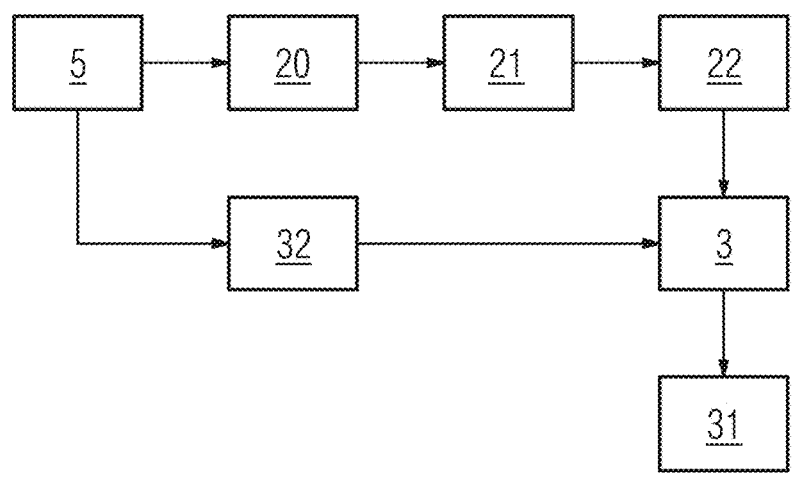

CONTROL UNIT FOR A MEDICAL IMAGING SYSTEM COMPRISING A PROCESSOR AND A LOGIC GATE; IMAGING SYSTEM AND METHOD FOR CONTROLLING A MEDICAL IMAGING SYSTEM

PRIORITY STATEMENT

The present application hereby claims priority under 35 U.S.C. § 119 to German patent application number DE 102018219878.0 filed Nov. 20, 2018, the entire contents of which are hereby incorporated herein by reference.

FIELD

Embodiments of the invention generally relate to a control unit for a medical imaging system; a medical imaging system and to a method for controlling a medical imaging system.

BACKGROUND

In control systems for medical imaging systems, control units of the type in question are often used as a "system-on-a-chip" (SoC). The control unit can comprise a microprocessor and a programmable logic gate. An example of such a medical imaging system is an X-ray system. The main task of such control systems consists, for example, in the closed-loop and/or open-loop control of current and voltage of an X-ray tube of the X-ray system and in controlling the rotational speed of a rotating anode of the X-ray tube. The control unit comprises for these tasks, for example, the programmable logic gate (field-programmable logic gate, FPGA for short). Suitable digital controllers and filters for performing the open-loop and/or closed-loop control can be implemented in the programmable logic gate.

Nominal values for the closed-loop and/or open-loop control, in particular for control loops of the closed-loop control, are usually transferred from an external control computer to the control unit. For example, the nominal values for an image acquisition are transferred before starting the image acquisition. In some acquisition modes, the nominal values are updated or changed during the image acquisition. Examples of this are readjusting a reference signal or executing a signal waveform.

The control system, in particular the control unit, is connected to the external control computer via an interface, in particular a standard interface, for instance CAN or Ethernet. In particular, the microprocessor provides this standard interface. Suitable control software, which runs on the microprocessor and indirectly controls the medical imaging system, uses device drivers provided by an operating system on the microprocessor to access the aforementioned interface, including the external control computer. Then the programmable logic gate is driven and/or controlled by the microprocessor in accordance with a command signal received via the interface. The programmable logic gate in turn performs open-loop and/or closed-loop control of the imaging system, taking into account the aforementioned driving and/or programming of the programmable logic gate.

The control unit can receive the nominal values, which were described in the introduction, as part of the command signal from the external control computer. In other words, the command signal comprises the nominal values.

SUMMARY

The inventors have discovered that the operating system, the drivers and/or the control software result in delays or latencies, which prevent any guarantee of the command signal being processed in real time, which is a requirement in certain cases. The microprocessor is therefore designed to drive the programmable logic gate in accordance with the command signal. In this process, the inventors have further discovered that the command signal must first be received and processed by the microprocessor, which can lead to the described delays or latencies.

At least one embodiment of the present invention is directed to a control unit for a medical imaging system, in particular an X-ray system, comprising:

a programmable logic gate designed for the closed-loop and/or open-loop control of at least one component of the medical imaging system, a microprocessor, which is connected to the programmable logic gate via a first interface, and a signal line for connecting the microprocessor to a contact array, which is arranged externally on the control unit, wherein the microprocessor is designed to provide a second interface via the signal line and to control the programmable logic gate in accordance with a command signal received via the second interface.

Another aspect of at least one embodiment of the invention relates to a medical imaging system, in particular an X-ray system, comprising the control unit described in the present application. Advantageous developments and advantages of embodiments of the control unit apply analogously also to the medical imaging system, in particular to the X-ray system, and are not described again here in the interests of brevity.

Another aspect of at least one embodiment of the invention relates to a method for controlling a medical imaging system by a control unit, which method comprises the steps:

a microprocessor of the control unit providing a second interface via a signal line, wherein the signal line connects the microprocessor to a contact array, which is arranged externally on the control unit;

the microprocessor receiving a command signal via the second interface;

the microprocessor controlling in accordance with the command signal received via the second interface a programmable logic gate of the control unit, which programmable logic gate performs open loop and/or closed loop control of at least one component of the medical imaging system.

Another aspect of at least one embodiment of the invention relates to a control unit for a medical imaging system, comprising:

a programmable logic gate, designed for at least one of closed-loop control and open-loop control of at least one component of the medical imaging system;

a microprocessor, connected to the programmable logic gate via a first interface; and a signal line to connect the microprocessor to a contact array, arranged externally on the control unit, the microprocessor being designed to provide a second interface via the signal line and to control the programmable logic gate in accordance with a command signal received via the second interface, the signal line being provided at least in part by the programmable logic gate, and the programmable logic gate including a receive unit for reading out the command signal.

Another aspect of at least one embodiment of the invention relates to a method for controlling a medical imaging system via a control unit, the method comprising:

providing, via a microprocessor of the control unit, an interface, the interface being provided via a signal line connecting the microprocessor to a contact array, arranged externally on the control unit;

receiving, via the microprocessor, a command signal through the interface;

controlling, via the microprocessor in accordance with the command signal received via the interface, a programmable logic gate of the control unit, programmable logic gate being configured to perform at least one of open loop control and closed loop control of at least one component of the medical imaging system, the signal line being provided at least in part by the programmable logic gate; and reading out the command signal via a receive unit of the programmable logic gate.

BRIEF DESCRIPTION OF THE DRAWINGS

FIG. 3 is a block diagram of a control arrangement for controlling a medical imaging system by a refined control unit;

FIG. 4 is a schematic overview of a processing flow for the refined control unit.

DETAILED DESCRIPTION OF THE EXAMPLE EMBODIMENTS

Figure 1:
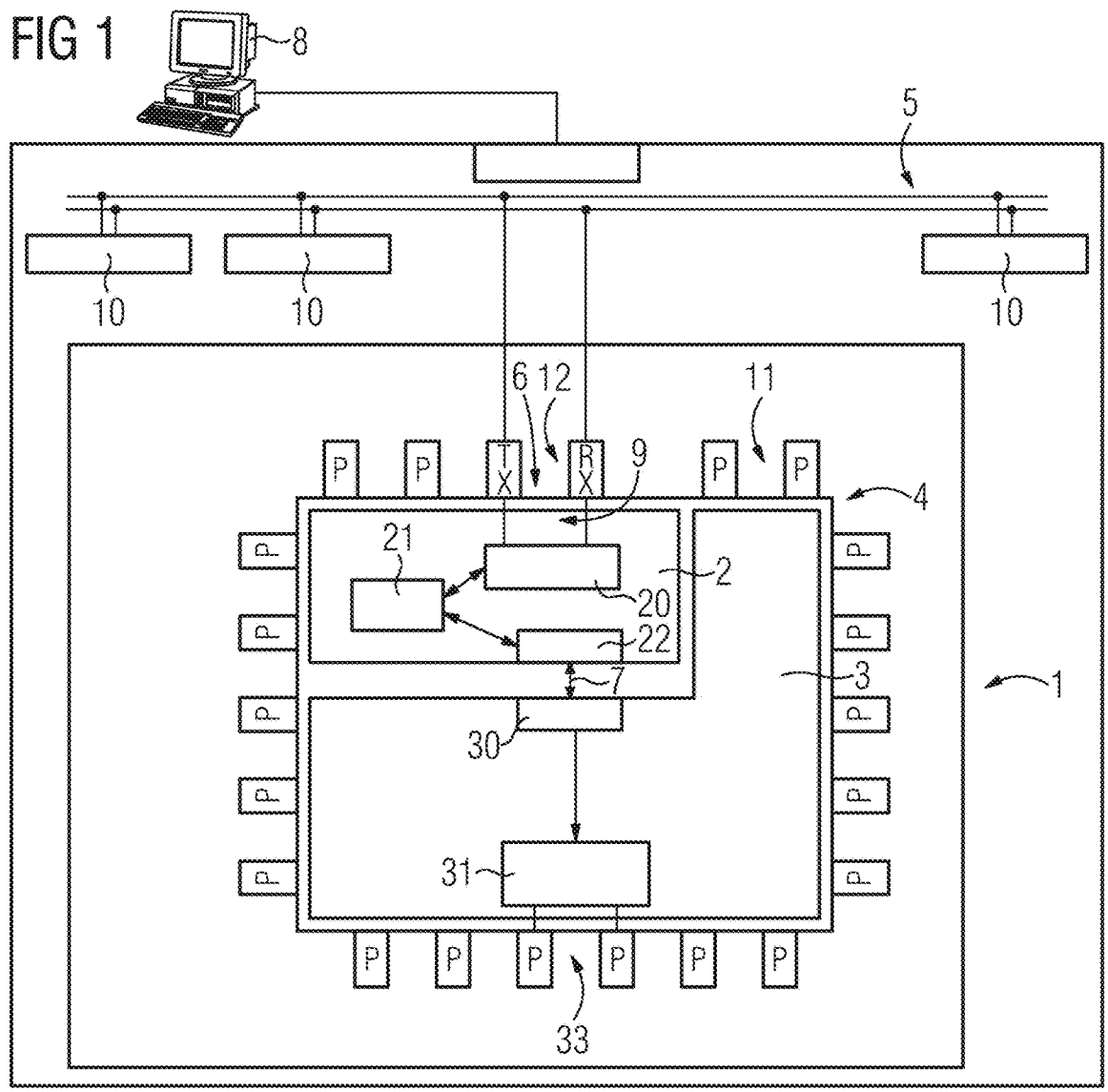
FIG. 1 is a block diagram of a control arrangement for controlling a medical imaging system by a control unit.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code.

Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention is directed to reducing the latency of open-loop and/or closed-control of a medical imaging system via a control unit.

At least one embodiment of the present invention is directed to a control unit for a medical imaging system, in particular an X-ray system, comprising:

a programmable logic gate designed for the closed-loop and/or open-loop control of at least one component of the medical imaging system, a microprocessor, which is connected to the programmable logic gate via a first interface, and a signal line for connecting the microprocessor to a contact array, which is arranged externally on the control unit, wherein the microprocessor is designed to provide a second interface via the signal line and to control the programmable logic gate in accordance with a command signal received via the second interface.

The second interface is intended in particular for communication with an external control computer. Thus the second interface can also be referred to as an external interface. The first interface is intended for communication between the microprocessor and the programmable logic gate. Therefore the first interface can also be referred to as an internal interface.

In order now to reduce the latency or avoid delays, according to at least one embodiment of the invention the signal line is provided at least in part by the programmable logic gate, and the programmable logic gate comprises a receive unit for reading out the command signal.

The signal line is fed at least in part through the programmable logic gate. In other words, the signal line is provided at least in part by conductor tracks and/or circuit elements, for instance transistors or logic components, of the programmable logic gate. The logic components may be AND gates, OR gates, Exclusive-OR gates or NOT gates, for example. The programmable logic gate may be what is known as a field-programmable gate array (FPGA). The signal line is fed or routed at least in part through the programmable logic gate, or more specifically the field-programmable gate array (FPGA). Contact with the microprocessor and/or the programmable logic gate can be made via the contact array and/or the signal line. In addition, power can be supplied to the control unit via the contact array. The receive unit is designed in particular to receive the command signal directly, i.e. as though the microprocessor were not connected in-between.

The microprocessor and the programmable logic gate can have a shared chip housing, also known as a package. The contact array can be arranged externally on the shared chip housing. Contact in particular with the microprocessor and the programmable logic gate can be made from outside the shared chip housing via the contact array. The contact array can comprise respective contacts, also known as pins, for the microprocessor and for the programmable logic gate. Said contacts of the microprocessor and of the programmable logic gate respectively are in particular connected solely to the associated control component in each case, i.e. to the microprocessor or to the programmable logic gate. The contacts can be embodied as general purpose input/output (GPIO for short) of the microprocessor or of the programmable logic gate respectively. For example, the signal line is connected at the contact array to contacts of the programmable logic gate, and in particular is not connected electrically to contacts of the microprocessor. The signal line can then be fed from the contacts of the programmable logic gate through the programmable logic gate to the microprocessor. For example, the control unit is embodied as a system-on-a-chip (SoC for short).

The receive unit can be designed to read out the command signal at least in part. "In part" in particular means that only certain commands of the command signal are read out by the receive unit. Alternatively, it can also be provided that the receive unit reads out all the commands of the command signal. For example, the logic gate is designed to read out the aforementioned nominal values from the command signal. Commands read out from the command signal, in particular the nominal values, can be applied directly by the programmable logic gate for the closed-loop and/or open-loop control of the medical imaging system. It is thereby possible to reduce the latency or avoid delays.

The outward communication (outward in relation to the control unit) via the second interface is performed in particular at least mainly or solely by the microprocessor. In other words, the receive unit does not communicate with the microprocessor or a further bus component, for instance the external control computer, connected to the second interface. The receive unit can be designed solely for passive reading out of data packets and/or command signals exchanged via the second interface. The command signal may be part of said data packets. Passive means here in particular that no communication whatsoever takes place with the further bus component and/or the microprocessor in this regard. Figuratively speaking, the command signal can be read out without the further bus component noticing. Obviously, there may also be more than one further bus component. In some embodiments, the receive unit is also designed to perform error correction and/or a plausibility check for the command signal and/or data packets. In this case, data packets and/or command signals that are implausible or identified as corrupted can be discarded. In general, error correction data read out as part of the data packets and/or of the command signal can be used for this purpose. This is done, for example, as part of a cyclical redundancy check (CRC). The receive unit can be designed to output an error signal to the microprocessor if an error is detected. This is also referred to as an interrupt.

According to a development of at least one embodiment, the microprocessor is designed to communicate with a terminal of a user via the second interface. The terminal of the user may be the external control computer, for instance. The command signal can be derived from a user input from the user. In other words, the second interface allows a user to control the control unit and thus indirectly the medical imaging system.

According to a development, for the purpose of providing the second interface, the microprocessor additionally has a direct signal line, which is not fed via the logic gate, wherein the direct signal line is disabled in favor of communication via the signal line in at least one operating state of the control unit. For instance, the direct signal line is a signal line that is fed from the microprocessor to contacts of the microprocessor at the contact array. In other words, the direct signal line can be fed directly to the microprocessor via contacts of the microprocessor. In contrast, the signal line that could also be designated the indirect signal line is fed, for example, from contacts of the programmable logic gate through the programmable logic gate to the microprocessor. A different operating mode can thereby be selected depending on the requirement.

According to a development of at least one embodiment, for the purpose of controlling the programmable logic gate and/or providing a second interface, the microprocessor is designed to run an operating system and/or a device driver. For example, the microprocessor can be configured by the device driver to form the second interface. For example, the microprocessor can be configured by the operating system to control the programmable logic gate. In contrast with the microprocessor, it can be provided that the programmable logic gate operates via a programmed hardware circuit. In other words, the open-loop or closed-loop control of the medical imaging system is performed in hardware by the programmable logic gate.

According to a development of at least one embodiment, the microprocessor is configured to influence the closed-loop and/or open-loop control of the medical imaging system by controlling the programmable logic gate. In other words, the microprocessor can change a principle of the closed-loop and/or open-loop control of the medical imaging system by controlling the programmable logic gate. The microprocessor achieves this in particular in a manner that is defined by the command signal. For example, the hardware circuit of the programmable logic gate is parameterized. It is thereby possible for the external control computer, for example, to parameterize and/or configure the programmable logic gate indirectly via the second interface.

According to a development of at least one embodiment, the signal line comprises, from the viewpoint of the microprocessor, a transmit line and a receive line, wherein the receive unit is connected solely to one of the two lines, in particular to the receive line. In other words, the signal line comprises a transmit line, which the microprocessor can use to send out data packets via the second interface, and a receive line, which the microprocessor can use to receive data packets and/or command signals via the second interface. In particular, the receive unit is connected to the receive line. In particular, the receive unit is not connected to the transmit line. The receive unit can thus have a design that is particularly efficient in terms of resources.

According to a development of at least one embodiment, the second interface is an Ethernet interface or part of a CAN bus. For example, the microprocessor is designed to establish an Internet connection via the second interface. Alternatively or additionally, the microprocessor is designed to establish a CAN connection via the second interface. For example, the microprocessor and the external control computer are nodes of the CAN bus. In contrast, the receive unit is advantageously not a node of the CAN bus but passively looks at data packets and/or command signals routed via the CAN bus. For example, the receive unit is embodied as what is known as a "sniffer". Specifically, the receive unit can be embodied as a "CAN sniffer".

According to a development of at least one embodiment, the programmable logic gate is designed to execute individual commands contained in the command signal directly, in particular without involving the microprocessor. The programmable logic gate is designed in particular to influence or to change the closed-loop and/or open-loop control of the medical imaging system at least to some extent directly according to the command signal, for instance according to individual commands contained therein. Individual commands can hence be used almost without delay, in particular dispensing with the detour via the microprocessor.

According to a development of at least one embodiment, the programmable logic gate is designed to provide a register, which can be accessed by the microprocessor, containing error information about errors that arise in the passive reading out of the command signal. Alternatively or additionally, the programmable logic gate can be designed to provide in an accessible manner to the microprocessor a general register. The programmable logic gate can be designed to provide in the register, data or logbooks (logs) essential to the operation of the programmable logic gate and/or of the receive unit. Said measures allow the microprocessor to monitor the proper operation of the programmable logic gate and to monitor the receiving, reading out and/or application of the command signal by the receive unit or by the programmable logic gate. This is necessary in particular because, unlike the prior art, the programmable logic gate can receive and/or apply the command signal at least to some extent independently, i.e. without interaction with the microprocessor.

According to a development of at least one embodiment, the microprocessor is designed to enable or disable the direct execution of the individual commands for the programmable logic gate. For example, the control unit has at least one operating mode in which, by way of an enable signal from the microprocessor, the programmable logic gate is able to execute individual commands directly. For example, the control unit has at least one operating mode in which, by way of a disable signal from the microprocessor, the programmable logic gate is unable to execute individual commands directly. In the latter operating modes, the direct execution of commands from the command signal is disabled for the programmable logic gate. The control unit can thereby be adapted to different underlying conditions.

According to a development of at least one embodiment, the command signal comprises real-time commands, which are commands to be followed in real time for the closed-loop and/or open-loop control of the medical imaging system, and comprises administration commands, which differ from said real-time commands, wherein the receive unit is designed only to read out the real-time commands. The real-time commands can comprise the aforementioned nominal values, for instance. For example, it is solely the real-time commands that are read out through the command signal and forwarded within the programmable logic gate for processing. For example, the receive unit is designed to discard the administration commands. In this case, the receive unit may be able to read out the administration commands briefly, with the receive unit being designed to discard the administration commands again directly after reading out, in particular without forwarding these commands. The administration commands can then be received and/or applied by the microprocessor.

According to a development of at least one embodiment, the programmable logic gate is designed for the closed-loop and/or open-loop control of an X-ray tube of the medical imaging system. In particular, the programmable logic gate is designed for the closed-loop and/or open-loop control of an acceleration voltage, of a current and/or of a rotation of a rotating anode of the X-ray tube. These are particularly time-critical parameters that can be controlled in a closed-loop and/or open-loop manner particularly reliably by programmable logic gates.

Another aspect of at least one embodiment of the invention relates to a medical imaging system, in particular an X-ray system, comprising the control unit described in the present application. Advantageous developments and advantages of embodiments of the control unit apply analogously also to the medical imaging system, in particular to the X-ray system, and are not described again here in the interests of brevity.

Another aspect of at least one embodiment of the invention relates to a method for controlling a medical imaging system by a control unit, which method comprises the steps:

a microprocessor of the control unit providing a second interface via a signal line, wherein the signal line connects the microprocessor to a contact array, which is arranged externally on the control unit;

the microprocessor receiving a command signal via the second interface;

the microprocessor controlling in accordance with the command signal received via the second interface a programmable logic gate of the control unit, which programmable logic gate performs open loop and/or closed loop control of at least one component of the medical imaging system.

An embodiment of the method is characterized in that the signal line is provided at least in part by the programmable logic gate, and the command signal is read out by a receive unit of the programmable logic gate.

In particular, the command signal that is read out influences the open-loop and/or closed-loop control of the at least one component by the programmable logic gate. In other words, the programmable logic gate can itself influence the open-loop and/or closed-loop control by way of the command signal.

Advantageous developments and advantages of the control unit and of the imaging system apply analogously also to the method according to embodiments of the invention, and vice versa.

FIG. 1 shows a control arrangement for controlling a medical imaging system, in particular an X-ray system. The control arrangement comprises a control unit 1, which comprises a microprocessor 2 and a programmable logic gate 3. The programmable logic gate 3 is in particular a field-programmable gate array (FPGA). The programmable logic gate 3 is designed to perform open-loop and/or closed-loop control of the medical imaging system. In particular, the programmable logic gate 3 is configured to control an acceleration voltage, current and/or rotational speed of a rotating anode of the imaging system in the form of an X-ray system. The advantage of using the programmable logic gate 3 for the control is a shorter delay, because the programmable logic gate 3 can perform the open-loop and/or closed-loop control in hardware.

The microprocessor 2 is intended to control the programmable logic gate 3. The microprocessor 2 is designed to provide a software environment 21. The software environment 21 may comprise an operating system and/or device drivers. Alternatively or additionally, the microprocessor 2 is designed to provide as part of the software environment 21 a software program product for controlling the programmable logic gate 3. In particular, this is what is known as a software application.

A first interface 7 is provided for the control of the programmable logic gate 3 by the microprocessor 2. The first interface 7 can also be referred to as an internal interface, because in the present case, the microprocessor 2 and the programmable logic gate 3 are part of a system-on-a-chip and therefore in particular are arranged in the same chip housing, also known as a package. In order to provide the first interface 7, the microprocessor 2 and the programmable logic gate 3 comprise respective bus components 22, 30 for providing the first interface 7.

In addition, the microprocessor 2 is designed to provide a second interface 6. The second interface 6 can also be referred to as an external interface, because the microprocessor 2 is designed to communicate with an external control computer 8 via the second interface 6. The second interface 6 is taken via a signal line 9 to a contact array 4, which is arranged externally on the control unit 1. In the present case, the signal line is provided by two single lines, namely a transmit line (TX) and a receive line (RX). The microprocessor 2 is linked directly to contacts 12 of the contact array 4 via the signal line 9, said contacts 12 being assigned solely to the microprocessor 2. The medical imaging system can be controlled indirectly, namely via the control unit 1, via the control computer 8. The microprocessor 2 is configured in particular to receive a control command from the external control computer 8 via the second interface 6. A bus system 5 is provided for communication via the second interface 6. The external control computer 8 and the control unit 1, or more precisely the microprocessor 2, are connected to each other by the bus system 5. Further nodes 10, in addition to the control unit 1 and the external control computer 8, can be connected to the bus system 5. The bus system 5 is a CAN bus or an Ethernet connection, for example. The microprocessor comprises a bus controller 20 for providing the second interface 6. The bus controller 20 may be, for example, a CAN controller or an Ethernet controller, for instance what is known as a MAC.

Figure 2:
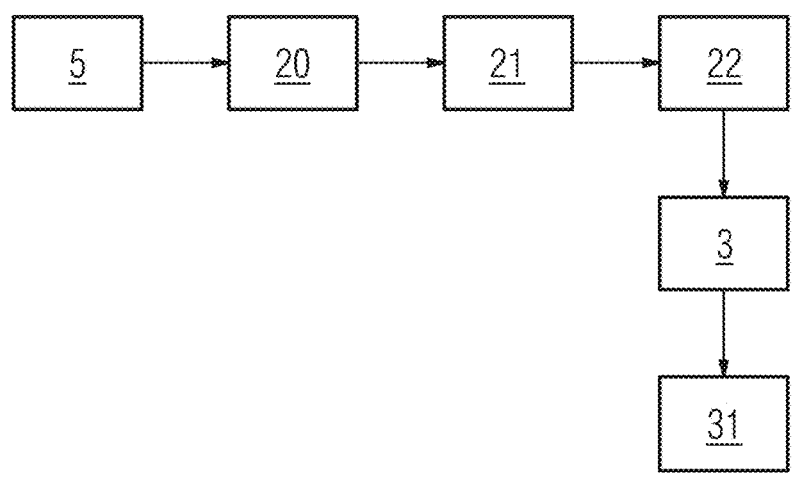
FIG. 2 is a schematic overview of a processing flow for the control unit.

FIG. 2 shows an example of a processing flow for controlling the programmable logic gate 3. On the basis of this control, the programmable logic gate 3 can in turn perform open-loop and/or closed-loop control of the medical imaging system.

The bus controller 20 receives a command signal from the bus system 5, or more precisely from the external control computer 8. The command signal is evaluated by the software environment 21. In particular, it is possible to derive from the command signal those open-loop and/or closed-loop control commands that are intended to be used by the programmable logic gate 3 for the open-loop and/or closed-loop control respectively of the medical imaging system. Alternatively or additionally, nominal values for the open-loop and/or closed-loop control can be derived from the command signal. Then the programmable logic gate 3 is driven accordingly via the first interface 7, or more precisely via the corresponding bus component 22 of the microprocessor 2. For example, the nominal values for the open-loop and/or closed-loop control are transferred to the programmable logic gate 3. For example, the nominal values can comprise values for the acceleration voltage, the current and/or the rotational speed of the rotating anode of the imaging system. Alternatively or additionally, the open-loop and/or closed-loop control commands can be transferred to the programmable logic gate 3, and/or the programmable logic gate 3 can be programmed in accordance with the open-loop and/or closed-loop control commands.

For example, the programmable logic gate 3 performs the open-loop and/or closed-loop control of the medical imaging system in accordance with the open-loop and/or closed-loop control commands and/or taking into account the nominal values. For this purpose, the programmable logic gate 3 comprises, for example, a controller 31, or the programmable logic gate 3 implements said controller 31. Corresponding open-loop and/or closed-loop control signals can be output via corresponding outputs 33 of the programmable logic gate 3.

The problem is that the command chain shown in FIG. 2 can cause problems as a result of delays. In particular, such delays can be caused by the software environment 21 provided by the microprocessor 2. The processing of the command signal from the external control computer 8 by the microprocessor 2 using the software environment 21 can result in greater latency or in delays. There is no guarantee of a real-time capability in the handover of the command signal to the programmable logic gate 3.

FIG. 3 shows an improved embodiment of the control unit 1. Unlike the embodiment shown in FIG. 1, in this case the signal line 9 is not fed directly from the contact array 4 to the microprocessor 2. Instead, at least portions of the signal line 9 are fed through the programmable logic gate 3. In other words, the signal line 9 is provided at least in part by the programmable logic gate 3. The signal line 9 connects the microprocessor 2, or more precisely its bus controller 20, to contacts 11 of the programmable logic gate 3. The contacts 11 of the programmable logic gate 3 are contacts that are assigned to the programmable logic gate 3. For example, the contacts 11 are linked electronically or logically solely to the programmable logic gate 3. The contacts 11 may be general purpose input/output (GPIO) pins of the programmable logic gate 3. In the present case, the signal line 9 is provided at least in part by conductor tracks of the programmable logic gate 3 and/or by circuit elements of the programmable logic gate 3.

A further signal line 13, also referred to as a direct signal line, can optionally be provided. The further signal line 13 connects the microprocessor 2, or its bus controller 20, to the contacts 12 of the microprocessor 2. In a normal state, however, this further signal line 13 may be disconnected by hardware or software (see reference sign 23).

The signal line 9 comprises a transmit line 36 and a receive line 35. The designation as a transmit line 36 or as a receive line 35 refers here to the microprocessor 2, or to its bus controller 20. The microprocessor 2, or its bus controller 20, is designed to receive data packets or command signals via the receive line 35. The microprocessor 2, or its bus controller 20, is designed to send out data packets or command signals via the transmit line 36.

A receive unit 32 of the programmable logic gate is connected to the receive line 35. This is where the present embodiment has an advantage over the embodiment of FIG.

1. By routing the signal line 9 via the programmable logic gate 3, the receive unit 32 can be connected to the signal line 9, or to the receive line 35.

The receive unit 32 is designed to read out data packets or command signals transferred via the receive line 35 to the microprocessor 2, or to its bus controller 20. If the bus system 5 is a CAN bus, then the receive unit 32 can be embodied as a "CAN sniffer". The receive unit 32 is designed to read out, at least in part, the command signal from the external control computer 8. For example, the receive unit 32 is designed to read out and directly apply specific commands, for instance real-time commands, which are to be followed in real time for closed-loop and/or open-loop control of the imaging unit. Alternatively or additionally, the receive unit 32 can be designed to extract from the command signal the aforementioned nominal values for controlling the imaging unit. The nominal values can then be applied directly. Obviously, the nominal values may be part of the real-time commands.

FIG. 4 shows an example of a processing flow in the improved embodiment shown in FIG. 3. Some commands continue to be transferred to the programmable logic gate 3 via the microprocessor 2, i.e. via the bus controller 20, the software environment 21 and bus component 22. In particular, these are general administration commands. In contrast, the real-time commands and/or the nominal values are read out directly by the receive unit 32 of the programmable logic gate 3. The real-time commands and/or the nominal values can then be forwarded to the controller 31 directly, i.e. bypassing the microprocessor 2. The controller 31 can take into account or apply the real-time commands and/or the nominal values in the open-loop and/or closed-loop control of the imaging system.

It is thereby possible to reduce delays or latencies, because the receive unit 32 causes shorter delays compared with the microprocessor 2. This is true in particular because, in order to operate, the receive unit 32 does not need the type of extensive software environment 21 that the microprocessor 2 does. In particular, the receive unit 32 works in hardware.

Figure 5:
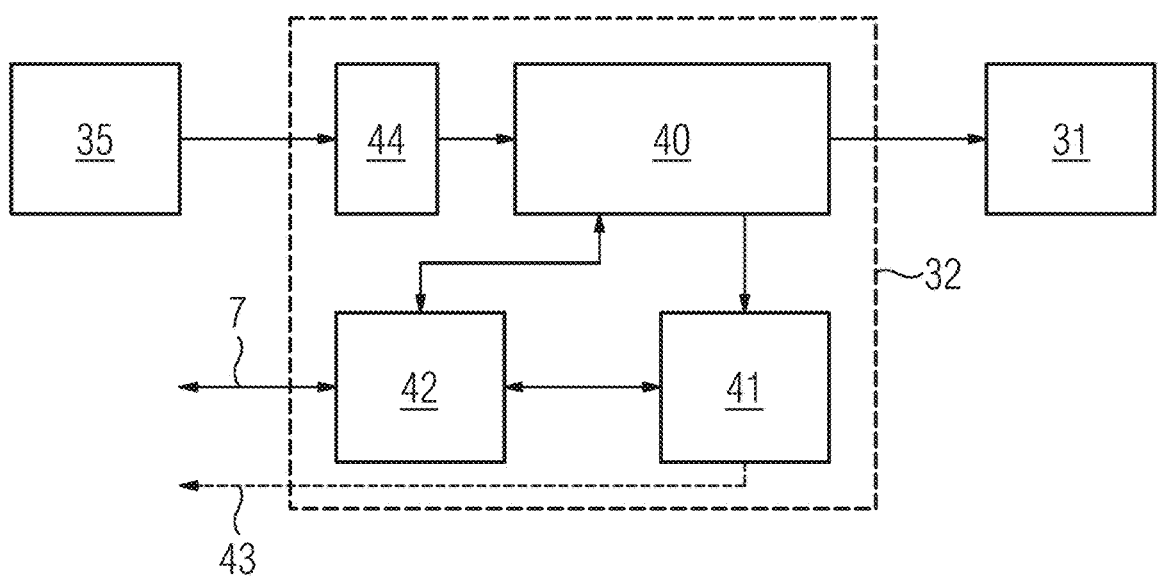
FIG. 5 is a block diagram of a receive unit of the refined control unit.

Finally, FIG. 5 shows a block diagram of the receive unit 32. The command signal is received from the receive line 35. On the input side, the receive unit 32 comprises an input filter 44. The input filter 44 can be designed to condition the input signal. Connected thereto is an extraction unit 40, which extracts data from the command signal for further processing. It can be provided that the extraction unit 40 discards commands and/or data packets that the receive unit 32 is not meant to process. These are administration commands, for instance. The extraction unit 40 can be designed to check the data extracted from the command signal. This is done, for example, using error correction data that is read out as part of the data packets and/or of the command signal. This is done in particular as part of a cyclical redundancy check (CRC).

The data intended for further processing may be the nominal values and/or real-time commands, for instance. In particular, the extraction unit 40 is designed to forward the data to the controller 31. The data is forwarded to the controller 31 in particular only when it has been established in the course of the error correction that this data is correct. In other words, data that is valid on the basis of the error correction is transferred to the controller 31 for further processing.

An optional error reporter 41, for instance an interrupt controller, can be designed to output an error signal 43 if an error is detected by the error correction. In other words, the receive unit 32 is designed to output the error signal 43. In particular, the error signal 43 is transferred to the microprocessor 2.

In addition, the receive unit 32 can provide a register 42. This register 42 can contain general status information. The receive unit 32 is designed, for example, to provide in the register 42, error messages, errors in respect of error correction, or general, acquired (logged) operating data for the receive unit 32.

In summary, it is shown how delays in the open-loop and/or closed-loop control of the medical imaging system can be reduced by feeding the signal line 9 via the programmable logic gate 3 in conjunction with the receive unit 32.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A controller for a medical imaging system, the controller comprising:
   a programmable logic gate configured to control at least one component of the medical imaging system via at least one of closed-loop control or open-loop control;
   a microprocessor connected to the programmable logic gate via a first interface; and
   a signal line connecting the microprocessor to a contact array arranged externally on the controller,
   wherein the microprocessor is configured to
      provide a second interface via the signal line, and
      control the programmable logic gate in accordance with a command signal received via the second interface,
   wherein the signal line is provided at least in part by the programmable logic gate, and
   wherein the programmable logic gate is configured to read out the command signal.

2. The controller of claim 1, wherein the microprocessor is configured to communicate with a terminal of a user via the second interface.

3. The controller of claim 1, wherein the microprocessor includes a direct signal line, the direct signal line not fed via the programmable logic gate, and
wherein the microprocessor is configured to disable the direct signal line in favor of communication via the signal line in at least one operating state of the controller.

4. The controller of claim 1, wherein the microprocessor is configured to run at least one of an operating system or a device driver for at least one of controlling the programmable logic gate or providing the second interface.

5. The controller of claim 1, wherein the microprocessor is configured to influence at least one of the closed-loop control or the open-loop control of the medical imaging system by controlling the programmable logic gate.

6. The controller of claim 3, wherein the signal line includes a transmit line and a receive line, and
wherein the programmable logic gate is connected solely to one of the receive line or the direct signal line.

7. The controller of claim 1, wherein the second interface is an Ethernet interface or part of a CAN bus.

8. The controller of claim 1, wherein the programmable logic gate is configured to provide a register, accessible by the microprocessor, containing error information about errors arising in reading out of the command signal.

9. The controller of claim 1, wherein the programmable logic gate is configured to execute individual commands contained in the command signal directly.

10. The controller of claim 9, wherein the microprocessor is configured to enable or disable direct execution of the individual commands for the programmable logic gate.

11. The controller of claim 1, wherein the command signal includes real-time commands and administration commands differing from the real-time commands, the real-time commands being commands to be followed in real time for at least one of the closed-loop control or the open-loop control of the medical imaging system, and
wherein the programmable logic gate is configured to only read out the real-time commands.

12. The controller of claim 1, wherein the programmable logic gate is configured to control an X-ray tube of the medical imaging system via at least one of the closed-loop control or the open-loop control.

13. A medical imaging system, comprising:
the controller of claim 1.

14. A method for controlling a medical imaging system via a controller, the method comprising:
providing, via a microprocessor of the controller, an interface via a signal line connecting the microprocessor to a contact array arranged externally on the controller, the signal line provided at least in part by a programmable logic gate;
receiving, via the microprocessor, a command signal through the interface;
controlling, via the microprocessor in accordance with the command signal, the programmable logic gate;
reading out, by the programmable logic gate, the command signal; and
controlling, via the programmable logic gate, at least one component of the medical imaging system via at least one of open loop control or closed loop control, the signal line being provided at least in part by the programmable logic gate.

15. The controller of claim 2, wherein the microprocessor includes a direct signal line, the direct signal line not fed via the programmable logic gate, and
wherein the microprocessor is configured to disable the direct signal line in favor of communication via the signal line in at least one operating state of the controller.

16. The controller of claim 2, wherein the microprocessor is configured to run at least one of an operating system or a device driver for at least one of controlling the programmable logic gate or providing the second interface.

17. The controller of claim 6, wherein the programmable logic gate is connected solely to the receive line.

18. The controller of claim 9, wherein the programmable logic gate is configured to execute individual commands involving the microprocessor.

19. The controller of claim 5, wherein the command signal includes real-time commands and administration commands differing from the real-time commands, the real-time commands being commands to be followed in real time for at least one of the closed-loop control or the open-loop control of the medical imaging system, and
wherein the programmable logic gate is configured to only read out the real-time commands.

20. The medical imaging system of claim 13, wherein the medical imaging system is an X-ray system.

21. The controller of claim 1, wherein at least a portion of the second interface is implemented by the programmable logic gate.

* * * * *